United States Patent [19]

Haydock

[11] Patent Number: 5,506,105

[45] Date of Patent: Apr. 9, 1996

[54] IN SITU ASSAY OF AMPLIFIED INTRACELLULAR MRNA TARGETS

[75] Inventor: Paul V. Haydock, Seattle, Wash.

[73] Assignee: Dade International Inc., Deerfield, Ill.

[21] Appl. No.: 216,233

[22] Filed: Mar. 22, 1994

Related U.S. Application Data

[63] Continuation of Ser. No. 808,456, Dec. 10, 1991, abandoned.

[51] Int. Cl.$^6$ .............................. C12Q 1/70; C12Q 1/68; C12P 19/34
[52] U.S. Cl. ........................ 435/6; 435/912; 435/91.21; 435/5; 935/16; 935/78
[58] Field of Search ................................ 435/6, 5, 91.21, 435/91.1; 935/16, 77, 78

[56] References Cited

PUBLICATIONS

Lawrence and Singer, *Nuc. Acids Res.*, 13:1777 (1985) Quantitative Analysis for the detection of actin gene expression.

Singer and Ward, *PNAS*, 79:7331 (1982). Actin gene expression visualized in chicken muscle tissue culture . . . .

Hafen et al., *EMBO Journal*, 2:617 (1983). An improved in sutu hybridization method for the detection of cellular . . . .

Brigati et al., *Virology*, 126:32 (1983). Detection of Viral Genomes in Cultured Cells and Paraffin-Embedded . . . .

Haase et al., *PNAS*, 87:4971 (1990). Application and detection of lentiviral DNA inside cells.

Fahy et al., Self-Sustained Sequence Replication (3SR): An Isothermal Transcription-Based Amplification System Alternative to PCR, *PCR Methods and Applications* 1:25-33 (1991). Self-sustained . . . .

Herrington et al., "Discrimination of closely homologous HPV types by nonisotopic in situ hybridization: definition and derivation of tissue melting temperatures." *Histochemical Journal* 22: 545-554 (1990).

Tecott, In Situ Hybridization, Applications to Neurobiology, K. L. Valentino et al Editors, 1987, Oxford University Press, New York, NY, pp. 1-24.

Gingeras, T. R. et al., Ann. Biol. Clin. (1990) 48:498-501.

Guatelli, J. C. et al., Proc. Natl. Acad Sci. USA (Mar. 1990) 87: 1874-1878.

Haydock, P. V and Radany, E. W., J. Cell Biol (Nov. 1990) 3: 57a (Abstract #298).

Haase, A. T. et al., Proc. Natl. Acad Sci USA (Jul. 1990) 87: 4971-4975.

Kwoh, D. Y and Kwoh T. J, Am. Biotechn. Lab. (Oct. 1990) 8: 14-25.

Veedorf, K. et al., Virology (1985) 145: 181-185.

*Primary Examiner*—Margaret Parr
*Assistant Examiner*—Carla Myers
*Attorney, Agent, or Firm*—Cynthia Tymeson; Kent Barta

[57] ABSTRACT

In an in situ hybridization assay, cells are fixed under conditions which preserve essential morphology, followed by transcription-based nucleic acid amplification of intracellular mRNA targets. The amplified targets are visualized by hybridizing labelled probes to the target sequences. The assay thereby provides a convenient method for detecting specific gene expression associated with morphologic characteristics of diagnostic significance.

2 Claims, 11 Drawing Sheets

HUMAN PAPILLOMAVIRUS TYPE 16 (HPV16), COMPLETE GENOME, 83-858
FILE ENZ, FROM 1 TO 776, MINIMUM CUTS 1, MAXIMUM CUTS 10,
MISMATCHES 0 CUTS

```
                              PpuMI
BB113                     H16-58
ATGCACCAAAAGAGAACTGCAATGTTTCAGGACCCACAGGAGCGACCCAGAAAGTTACCA   60
                                                        BB4

CAGTTATGCACAGAGCTGCAAACAACTATACATGATATAATATTAGAATGTGTGTACTGC  120

AAGCAACAGTTACTGCGACGTGAGGTATATGACTTTGCTTTTCGGGATTTATGCATAGTA  180

TATAGAGATGGGAATCCATATGCTCTATGTGATAAATGTTTAAAGTTTTATTCTAAAATT  240

AGTGAGTATAGACATTATTGTTATAGTTTGTATGGAACAACATTAGAACAGCAATACAAC  300

AAACCGTTGTGTGATTTGTTAATTAGGTGTATTAACTGTCAAAAGCCACTGTGTCCTGAA  360

GAAAAGCAAAGACATCTGGACAAAAAGCAAAGATTCCATAATATAAGGGGTCGGTGGACC  420

GGTCGATGTATGTCTTGTTGCAGATCATCAAGAACACGTAGAGAAACCCAGCTGTAATCA  480
                                                     BB114
BB111
TGCATGGAGATACACCTACATTGCATGAATATATGTTAGATTTGCAACCAGAGACAACTG  540

BB109
ATCTCTACTGTTATGAGCAATTAAATGACAGCTCAGAGGAGGAGGATGAAATAGATGGTC  600

CAGCTGGACAAGCAGAACCGGACAGAGCCCATTACAATATTGTAACCTTTTGTTGCAAGT  660

GTGACTCTACGCTTCGGTTGTGCGTACAAAGCACACACGTAGACATTCGTACTTTGGAAG  720
                   BB112
              H16-686
ACCTGTTAATGGGCACACTAGGAATTGTGTGCCCCATCTGTTCTCAGAAACCATAA      776
              H16-743                       H16-773
```

FIG.3

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
  ( A ) LENGTH: 776 base pairs
  ( B ) TYPE: nucleic acid
  ( C ) STRANDEDNESS: unknown
  ( D ) TOPOLOGY: unknown ( i i ) MOLECULE TYPE: DNA (genomic)

( x i ) SEQUENCE DESCRIPTION: SEQ ID NO:1:

```
ATGCACCAAA  AGAGAACTGC  AATGTTTCAG  GACCCACAGG  AGCGACCCAG  AAAGTTACCA    60
CAGTTATGCA  CAGAGCTGCA  AACAACTATA  CATGATATAA  TATTAGAATG  TGTGTACTGC   120
AAGCAACAGT  TACTGCGACG  TGAGGTATAT  GACTTTGCTT  TTCGGGATTT  ATGCATAGTA   180
TATAGAGATG  GGAATCCATA  TGCTGTATGT  GATAAATGTT  TAAAGTTTTA  TTCTAAAATT   240
AGTGAGTATA  GACATTATTG  TTATAGTTTG  TATGGAACAA  CATTAGAACA  GCAATACAAC   300
AAACCGTTGT  GTGATTTGTT  AATTAGGTGT  ATTAACTGTC  AAAAGCCACT  GTGTCCTGAA   360
GAAAAGCAAA  GACATCTGGA  CAAAAAGCAA  AGATTCCATA  ATATAAGGGG  TCGGTGGACC   420
GGTCGATGTA  TGTCTTGTTG  CAGATCATCA  AGAACACGTA  GAGAAACCCA  GCTGTAATCA   480
TGCATGGAGA  TACACCTACA  TTGCATGAAT  ATATGTTAGA  TTTGCAACCA  GAGACAACTG   540
ATCTCTACTG  TTATGAGCAA  TTAAATGACA  GCTCAGAGGA  GGAGGATGAA  ATAGATGGTC   600
CAGCTGGACA  AGCAGAACCG  GACAGAGCCC  ATTACAATAT  TGTAACCTTT  TGTTGCAAGT   660
GTGACTCTAC  GCTTCGGTTG  TGCGTACAAA  GCACACACGT  AGACATTCGT  ACTTTGGAAG   720
ACCTGTTAAT  GGGCACACTA  GGAATTGTGT  GCCCCATCTG  TTCTCAGAAA  CCATAA       776
```

( 2 ) INFORMATION FOR SEQ ID NO:2:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:2:

```
ATGCATGGAG  ATACACCTAC  ATTG                                              24
```

( 2 ) INFORMATION FOR SEQ ID NO:3:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear (  i i  ) MOLECULE TYPE: DNA (genomic)

(  x i  ) SEQUENCE DESCRIPTION: SEQ ID NO:3:

GCACAACCGA AGCGTAGAGT CACA                    24

( 2 ) INFORMATION FOR SEQ ID NO:4:

(  i  ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear (  i i  ) MOLECULE TYPE: DNA (genomic)

(  x i  ) SEQUENCE DESCRIPTION: SEQ ID NO:4:

ATGCACCAAA AGAGAACTGC AATG                    24

( 2 ) INFORMATION FOR SEQ ID NO:5:

(  i  ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear (  i i  ) MOLECULE TYPE: DNA (genomic)

(  x i  ) SEQUENCE DESCRIPTION: SEQ ID NO:5:

CAGCTGGGTT TCTCTACGTG TTCT                    24

( 2 ) INFORMATION FOR SEQ ID NO:6:

(  i  ) SEQUENCE CHARACTERISTICS:
  ( A ) LENGTH: 26 base pairs
  ( B ) TYPE: nucleic acid
  ( C ) STRANDEDNESS: single
  ( D ) TOPOLOGY: linear (  i i  ) MOLECULE TYPE: DNA (genomic)

(  x i  ) SEQUENCE DESCRIPTION: SEQ ID NO:6:

GGACCCACAG GAGCGACCCA GAAAGT                  26

( 2 ) INFORMATION FOR SEQ ID NO:7:

(  i  ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear (  i i  ) MOLECULE TYPE: DNA (genomic)

(  x i  ) SEQUENCE DESCRIPTION: SEQ ID NO:7:

TCTGAGAACA GATGGGGCAC ACAA                    24

( 2 ) INFORMATION FOR SEQ ID NO:8:

(  i  ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear (  i i  ) MOLECULE TYPE: DNA (genomic)

(  x i  ) SEQUENCE DESCRIPTION: SEQ ID NO:8:

```
GTGTGCCCAT TAACAGGTCT TCCA                                                  24
```

( 2 ) INFORMATION FOR SEQ ID NO:9:

( i ) SEQUENCE CHARACTERISTICS:
    ( A ) LENGTH: 24 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:9:

```
ACAACCGAAG CGTAGAGTCA CACT                                                  24
```

( 2 ) INFORMATION FOR SEQ ID NO:10:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:10:

```
TAACTTTCTG GGTCGCTCCT GTGGGTCCTG                                            30
```

( 2 ) INFORMATION FOR SEQ ID NO:11:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:11:

```
ATAGATGGTC CAGCTGGACA AGCAGAACCG                                            30
```

( 2 ) INFORMATION FOR SEQ ID NO:12:

( i ) SEQUENCE CHARACTERISTICS:
    ( A ) LENGTH: 22 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:12:

```
AATTTAATAC GACTCACTAT AG                                                    22
```

IN SITU ASSAY OF AMPLIFIED INTRACELLULAR MRNA TARGETS

This is a continuation, of application Ser. No. 07/808,456, filed on Dec. 10, 1991, now abandoned.

BACKGROUND OF THE INVENTION

In situ hybridization assays have become increasingly important diagnostic tools in evaluating a variety of pathologic conditions. The technique combines the classical efficacy of morphologic visualization of a selected cell population with the ability to simultaneously detect the presence and/or expression of specific genes.

An early paper, Lawrence and Singer, *Nuc. Acids Res.*, 13: 1777 (1985) describes the use of plasmid probes, isotopically labelled, in detecting action gene expression. This paper also describes experiments for optimizing the pretreatment conditions in preparing cells for in situ hybridization. It was found that pretreatment with 5% proteinase K followed by immersion in 2% paraformaldehyde permitted satisfactory hybridization without undue distortion of cellular morphology. A nonisotopic probe detection system for action gene expression was reported by Singer and Ward, *PNAS*, 79: 7331 (1982).

The sensitivity of in situ hybridization was evaluated by Hafen, et al., *EMBO Journal*, 2: 617 (1983). Utilizing a tritiated probe, it was possible to detect about 100 complementary RNA molecules per cell after three days of autoradiographic exposure. Brigati et al., *Virology*, 126: 32 (1983) demonstrated the feasibility of using biotinylated probes in an in situ hybridization assay of paraffin block specimens coupled to immunohistochemical detection mediated by horseradish peroxidase. For a detailed review of the applications of in situ hybridization, see In Situ *Hybridization, Principles and Practice*, eds. Polak & McGee, Oxford University Press, 1990.

Of particular interest is the use of in situ hybridization techniques in the investigation of human papilloma virus (HPV) infections, and the role of the virus in transformation of cervical cells. Herrington, et al. demonstrated that in situ hybridization was capable of discriminating among closely homologous HPV types 6 and 11. However, these investigators found that hybridization conditions in solution and in situ were very different, and kinetic equations derived from solution data were not predictive of the hybridization properties of selected probes in situ.

The inherent limitation in this and other assay techniques based on direct hybridization of native RNA or DNA with labelled probes is copy number. If the number of target molecules present in cells is very low, on the order of less than 100 to 1000, then the risk of a false negative test is very great. In order to overcome this limitation, Haase et al., *PNAS*, 87: 4971 (1990) recently employed the technique of polymerase chain reaction (PCR) to amplify the low copy number of certain lentiviruses present in cells, so that sufficient target is available for hybridization and subsequent visualization. While this technique was shown to overcome the problem of low copy number, it is also evident that significant natural morophology is destroyed because of the harsh temperature shifts between 65° C. and 95° C. involved in PCR cycling.

SUMMARY OF THE INVENTION

The present invention provides for the first time an in situ hybridization assay for detection of low copy number RNA targets under conditions which preserve essential cell morophology. In accordance with this method, cells are first fixed onto a surface such as a glass slide, or embedded in a paraffin block, and permeabilized to permit inward diffusion of enzymes, primers hybridizable to sequences flanking a target RNA sequence, substrates, and other reagents required in nucleic acid amplification, under conditions which maintain morphological integrity of the cells.

An amplification reaction of the type referred to as self-sustained sequence amplification reaction (3SR) is then carried out at mild temperatures of generally less than 45° C. The amplified target is then probed with a labelled nucleic acid sequence complementary to all or a portion of the amplified interprimer target sequence. After a wash to remove unhybridized probe, the remaining duplexes are developed and visualized. In a preferred embodiment, probe nucleic acids are conjugated to an enzyme such as horseradish peroxidase, to which is added a chromogenic or fluorogenic substrate. The presence of specifically amplified target is clearly visible as a colored region in the location of the cytoplasm of the fixed cells under conventional light or fluorescence microscopy.

More particularly, the steps of the present assay method comprise fixing selected cells to a support, which includes embedding in a paraffin block, treating the cells with a permeabilizing agent such as proteinase K, pronase, or other protease of similar specificity, adding amplification reagents omitting dimethylsulfoxide (DMSO) and including deoxyribonucleotide and ribonucleotide triphosphates, an enzyme mix having reverse transcriptase and RNAse H activities, and a DNA dependent RNA polymerase, a first primer complementary to a target RNA sequence having at its 3' end a promoter sequence operable to the DNA dependent RNA polymerase, a second primer complementary to the opposite strand of the target at an interprimer interval of minimally 400 bases, and a suitable buffer, incubating the cells at a temperature of less than 45° C. to 50° C. for a time sufficient to allow 3SR amplification of the interprimer target region to occur, adding a labelled probe complementary to a sequence contained in the amplified interprimer target sequence, washing the cells to remove excess unhybridized probe, and visualizing the labelled probe-target duplexes under a microscope.

In a preferred embodiment, cervical cells suspected of harboring HPV are assayed utilizing the present method in which primer pairs are selected which specifically amplify mRNA being transcribed from the E6/E7 region of the HPV genome. Since expression of E6/E7 occurs only in cells actually transformed to the malignant state, this assay is specific for the detection of early malignancy. This is a significant improvement over existing tests which only detect the presence of genomic HPV DNA, and not actual intracellular viral expression indicative of a disease state.

The selection of primers for any transcribably expressed genetic marker in an in situ hybridization assay comprises randomly selecting primer sequences of about 8 to 24 nucleotides in a 5' portion of a target region of a transcribed gene contained in cells, randomly selecting primer sequences upon an opposite complementary sequence of the target region of the transcribed gene, a promoter operably linked to the second primer or the first primer, or both, with the interprimer distance being at least 400 nucleotides, amplifying by a 3SR substantially isothermal amplification technique the interprimer target region, visualizing by probe hybridization, and first comparing the first primer amplification incorporating individually the series of second primers, and secondly comparing the most highly amplified of the second primer in pairwise reaction, and finally, selecting the first and second primers which give a level of amplification at least equal to three logs amplification of target gene per original copy.

BRIEF DESCRIPTION OF THE DRAWINGS

FIG. 3 is a nucleic acid description indicating the position of various primers and probes.

DETAILED DESCRIPTION OF THE PREFERRED EMBODIMENT

Figure 1:
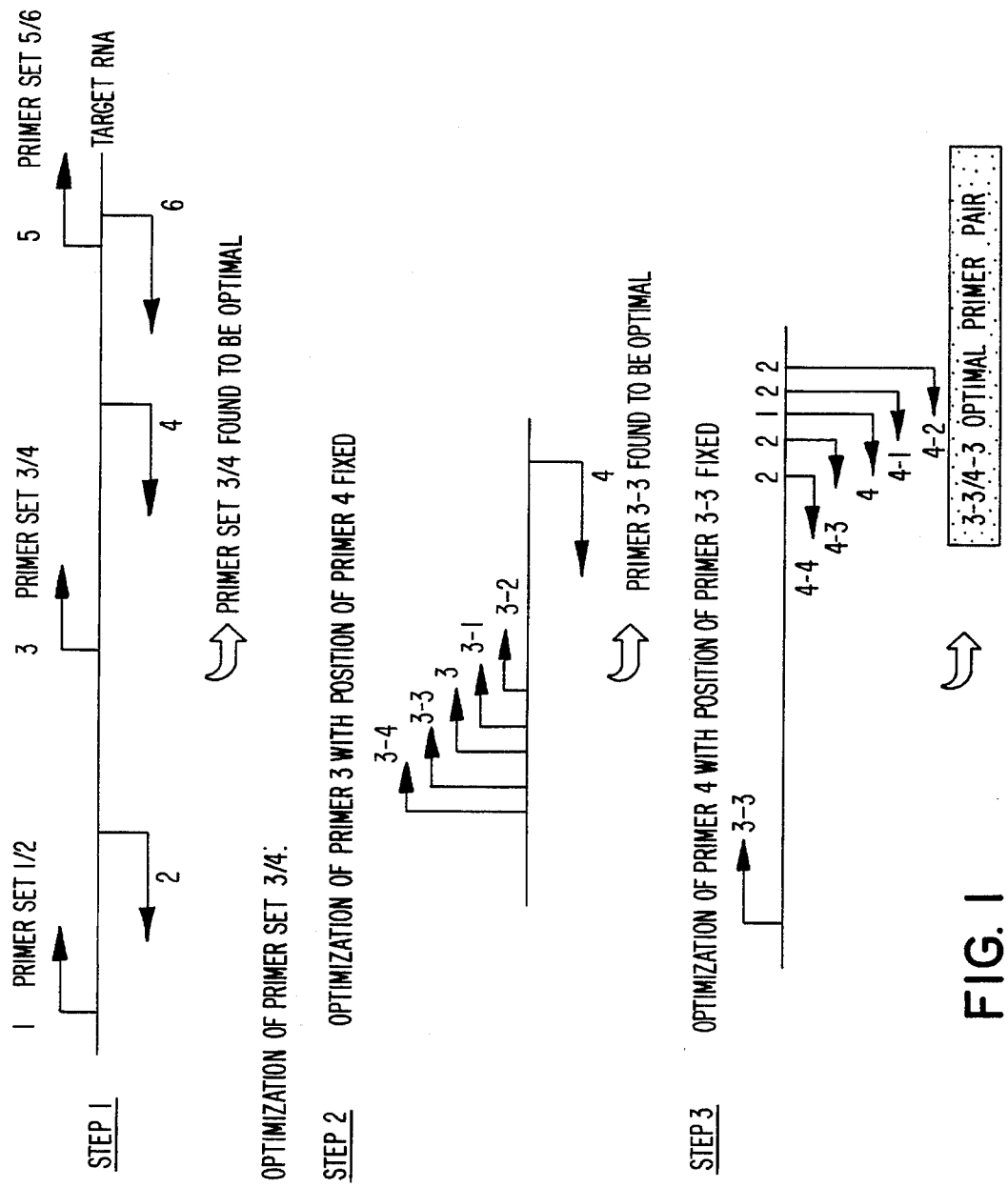
FIG. 1 is a schematic showing the relative position of various primer pairs utilized in amplifying HPV markers.

Nearly all in situ hybridization assays described heretofore rely upon sufficient copy number of the target sequence to be present for satisfactory visualization. However, in situations wherein copy number is very low, on the order of less than 100, no signal or a background level signal may be detected. It is therefore desirable to amplify the target copy number to a level where visualization is feasible. Self-sustained sequence replication (3SR) is clearly the method of choice since the complete reaction is conducted at substantially isothermal temperatures between about 37° C. and 50° C. The reaction is carried out essentially as described in Fahy et al., *Self-Sustained Sequence Replication (3SR): An Isothermal Transcription-Based Amplification System Alternative to PCR, PCR Methods and Applications*, 1: 25–33 (1991) or as modified for use with a lytic bacteriophage DNA polymerase as disclosed in my copending application Ser. No. 7/750,805, filed Aug. 27, 1991.

By substantially isothermal, it is meant that the temperature may be varied over the course of an approximately one hour reaction time within the temperature range of about 37° C. to 50° C. Alternatively, one temperature may be selected to carry out the entire reaction. 3SR amplification at 45° C. is preferred. The relatively mild reaction conditions, in contrast to the high temperature cycling used in PCR, is essential to preservation of the essential morphology of the cells.

The cells may be fixed by any method known in the art which does not involve treatments leading to cellular enucleation, or cell membrane damage resulting in exudation of cytoplasm. In particular, membrane disrupting agents such as detergents or other surfactants should be carefully avoided. Standard dessication methods utilizing ethanol or ethanol/acetic acid may be used, with ethanol alone being somewhat better. In the preferred embodiment, fixation is achieved with paraformaldehyde, as set forth in the Examples.

As part of the cell fixation process, it is essential to achieve permeabilization without disruption or distortion of essential cell morphology. "Essential" cell morphology means that cell shape, staining characteristics, and internal structure are sufficiently preserved so that an accurate and correct identification of the cell type and its pathological characteristics can be made. It is found that the permeabilization step in the present method is critical. Too much permeability results in loss of essential morphology and diffusion out of the cell of duplex probe-amplified nucleic acid structures indicative of a positive test. Detergents, DMSO, or other reagents known to disrupt lipid components of cell membranes are to be strictly avoided.

I have determined empirically that satisfactory permeabilization of cells can be achieved by treatment thereof solely with a protease such as protease K, pronase, or other protease of similar specificity. The range of treatment conditions is generally from 0.5 to 12 ug/ml at 30°–37° C. for a period of 5 to 20 minutes. For cell smears on glass slides, treatment with protease K or pronase at a concentration of 1 ug/ml at 37° C. for 10 minutes is highly satisfactory. For cells embedded in paraffin blocks, somewhat higher concentrations of protease in the 10 ug/ml range are preferred.

It will be appreciated that the permeabilizing conditions for different types of cells and under different conditions of fixation may vary within the ranges herein specified. It is suggested that a practitioner of the present method initially test permeabilization of target cells at 0.5, 1.0, 1.5, 5.0, and 10.0 ug/ml at 37° C. for 10 minutes to establish in this simple format the optimum concentration of protease for the type of target cells selected. It is also recommended that every assay of the present method include known positive and negative control specimens.

In the typical 3SR amplification system, it is well known that inclusion of approximately 10% dimethylsulfoxide (DMSO) is necessary for satisfactory amplification. It is believed that DMSO relaxes secondary structure of the RNA target, thereby permitting a greater level of polymerase initiation and extension. In the in situ hybridization disclosed herein, inclusion of DMSO is to be avoided. It is found that amplification is considerably impaired in the presence of DMSO.

In practicing the present invention, care must be taken to ensure that only targets larger than 400 bases are amplified. At sizes of less than about 400 bases, there is an apparent tendency for the target sequences and/or their probe hybridization duplexes to diffuse out of cells during the wash step, leading to false negative results. In 3SR amplification targets are generally selected over relatively short nucleotide spans of less than 400 bases, because the reverse transcriptase is thought to be poorly processive and inefficient in second strand synthesis in thich the RNA-DNA duplex is converted to ds DNA. The practical upper bound for classical 3SR is about 700 nucleotides. Thus, the transcription-based amplification disclosed in the copending application, supra, is preferred for larger targets of greater than 650 nucleotides and is mandatory for any target over about 1000 bases.

The primers utilized in the insitu amplification assay are preferably about 8 to 30 nucleotides long. It has frequently been observed that some primer pairs are more efficient than others in supporting amplification. This phenomenon does not appear to be related entirely to secondary structure of the primer or its complementary sequence. Similarly there does not appear to be any specific pattern of base distribution that allows prediction of primer efficacy. It is apparent, however, that both primers are involved in amplification efficiency.

Since it is impossible to test every possible combination of primers for a given target region, the following method has been developed to identify primer pairs giving satisfactory 3SR amplification. A target region is selected which contains at least 400 nucleotides and flanking regions from which primer sequences are to be selected. A series of primer sequences from each flanking region on the complementary strands are randomly selected. The first strand primer is then pairwise tested in a solution amplification reaction against each of the randomly selected second complementary strand primers.

The best second primer is then tested pairwise against each of the first primer series. After comparing the results of all the pairwise combinations, the best primer pair is then selected for amplifications of the minimally 400 base interprimer region. Levels of amplifcation 3 logs or more have diagnostic utililty, but ordinarily levels of insitu amplification in excess of 6 logs are achieved. The term "interprimer region" is defined as the nucleotide span lying between the 5' position of the annealed first primer and the 5' position of the second primer annealed to the opposite complementary strand.

Utilizing this method and the insitu amplification assay system hereinabove described, an insitu assay was developed for HPV infected cells, as follows:

FIG. 1 describes a method to choose optimal primer pairs for 3SR amplification. The target RNA can be from any source. The 3SR reaction requires 2 primers, one of which must contain the T7 RNA polymerase binding site. Not every primer pair functions efficiently in 3SR. The method outlined in FIG. 1 is a purely empirical method as a theoretical basis for 3SR primer selection has yet to be established.

In step 1, several primer sets are synthesized which would amplify different segments of the target RNA (referred to at ½, ¾, ⅝ in FIG. 1). Each set is assayed in the 3SR reaction. Products can be analyzed by any means which results in at least a semiquantitative estimation of the efficiency of each primer pair. At least one primer pair will support 3SR amplification. If one is not found, this step is repeated until a primer set is found.

For the example given, assume set ¾ is the best set. Primer 4 is held fixed while a set of primers are synthesized whose positions differ from that of primer 3 (designated 3-1, 3-2, 3-3, 3-4 in FIG. 1). These primers are likewise assayed in 3SR and analyzed.

For the example given, assume primer 3-3 is optimal. In step 3, the primer at position 3-3 is held fixed, and a series of primers is synthesized as described above which vary in position from primer 4 by 1-4 basis. These primers are assayed in 3SR and analyzed. One primer set will yield optimal amplification.

Figure 2:
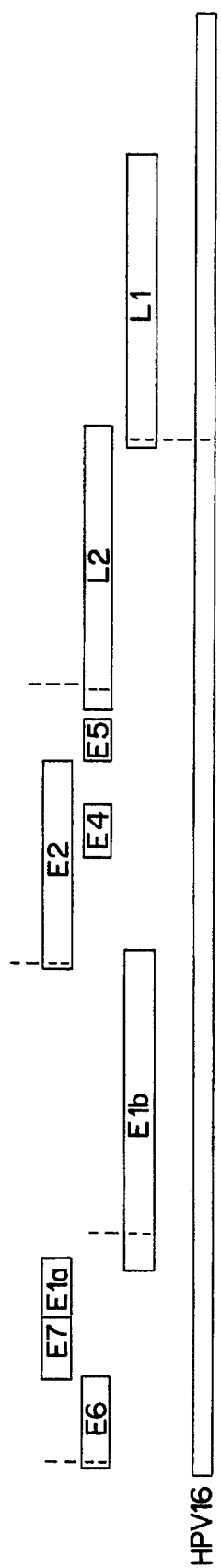
FIG. 2 is a schematic showing the genomic organization of various human papilloma viruses.

FIG. 2 refers to a map of the organization of the genome of human papillomavirus type 16. The region of interest involves the genes responsible for transformation which are the E6/E7 genes.

FIG. 3 refers to the specific sequence of the E6/E7 region of HPV16 (SEQ ID NO:1). This sequence notes the positions by coextensive lines drawn above or below the designated sequence of the relevant oligonucleotides as listed in Table 1 hereinbelow.

EXAMPLE 1

General Procedures Applicable to All Examples

In Situ 3SR Amplification (1) Slide preparation i. SiHa, HeLa, and HF fibroblast cultures are prepared. Cells are trypsinized from plate, suspended in 10 ml media and counted.

ii. Prepare a mix of SiHa/HF or HeLa/HF at an 80:20 ratio (approximately).

iii. In 8 well Lab-Tek chamber slides, plate 0.4 ml of cell suspension.

iv. Grow cells overnight at 37° C.

(2) Fixation i. Preparation of Paraformaldehyde Fix

A. Mix 1.6 g paraformaldehyde with 20 ml $H_2O$. Heat 30 seconds in microwave.

B. Add 20 ul 2N NaOH. Swirl to dissolve. Heat in microwave 20–30 seconds.

C. Add 20 ml 2× buffer (2× PBS, 10 $MgCl_2$).

ii. Remove plastic chimney from each slide but leave gasket in place. Rinse slide 2× in PBS.

iii. Remove slides to Paraformaldehyde for 5 minutes.

iv. Rinse slides in PBS.

v. Dehydrate slides through an alcohol series (30, 60, 80, 95%, 100%). Air dry slides and store dessicated at 4° C.

(3) Pretreatments i. Rehydrate slides through an alcohol series into 2× SSC.

ii. Incubate slides in 20 mM Tris pH 7, 2 mM $CaCl_2$, 1 ug/ml Proteinase K for 15 minutes at 37° C. (Optimized.)

iii. Transfer slides to 0.2M Tris pH 7 0.1M glycine for 10 minutes at room temperature.

iv. Rinse slides briefly in 2× SSC and amplify.

(4) Amplification i. Prepare an amplification mix on ice. For each amplification.

| 5× Buffer | 20 ul |
|---|---|
| 5× NTPs | 20 ul |
| Primer 113 | 5 ul (optimized) |
| Primer 112 | 5 ul (optimized) |
| $H_2O$ | 45 ul |
| AMV RT | 1.5 ul |
| T7 RNA polymerase | 1 ul |
| RNaseH (1 u/ul) | 1 ul (optimized) |

Pipet this mix directly onto the cells.
Incubate in a humid chamber at 37° C. for 2 hours.

ii. Stop by rinsing slides briefly in 2× SSC.

iii. Transfer slides to 4% paraformaldehyde for 15 minutes.

iv. Rinse slides in 2× SSC.

(5) Detection i. Hybridization Mix:

| 2× hybrid mix | 50 (12× SSC, 10× DEN, 200 ug/ml ssDNA) |
|---|---|
| IM DTT | 2 |
| $H_2O$ | 50 |
| probe | 100 mg (HRP labelled BB4) (HRP labelled oligo) |

Add this mix to each slide.

ii. Incubate 1 hour at 37° C.

iii. Wash 2× in 2× SSC for 10 minutes.

iv. Transfer slides to 0.5 mg/ml DAB (50 mg DAB in 100 ml PBS. Add 10 ml 1% $NiCl_2$ and 15 ul 30% $H_2O_2$). Incubate up to 15 minutes at room temperature.

v. Wash 3× in $H_2O$ to stop reaction.

(6) Silver Enhancement:

i. Prepare 2 solutions.

A. 50 g $Na_2CO_3$ (1 l)

B. 2 g $AgNO_3$ (1 l, $H_2O$), 2 g $NH_4NO_3$, 10 g tungstosilic acid, 7 ml 40% formaldehyde. Store solutions at 4° C.

ii. To use, mix equal volumes A and B just before use.

iii. Incubate slides in this up to 15 minutes.
iv. Stop with 1% HOAc.
v. Rinse with H$_2$O.
vi. Counterstain, dehydrate, and coverslip.

Growth Media for SiHa

85% EMEM (Eagle's minimum essential medium with non-essential amino acids and sodium pyruvate)
15% fetal bovine serum

Preparation of HRP Conjugate

Conjugates were prepared by the method of Li et al., *Nuc. Acids Res.*, 15: 5275 (1987) with the following modifications:

(1) dithio-bu-propionyl-NHS modification of the 3' N-linked oligonucleotide, and Bromo-acetyl-NHS modification of horseradish peroxidase was performed in 0.1M NaHCO$_3$ pH10.

(2) The derivatized oligonucleotide was purified from excess reagent by 2 sequential ethanol precipitations in the presence of lithium chloride.

(3) Derivatized horseradish peroxidase was purified from excess reagent by 2 sequential ethanol precipitations.

(4) Conjugations were performed in 100 ul total volume.

(5) Conjugates were purified from unreacted oligonucleotide by chromotography on Sephadex G75SF in 50 mM Tris pH 7.5.

| Source of Cell Lines | | |
|---|---|---|
| Cell Line or Virus | Accession # | Source |
| HPV16 | 38687 | GenBank |
| Hela | CCL2 | ATCC |
| SiHa | HTB35 | ATCC |
| Human Fibroblast | SP131029-1a | Baxter/Bartels |

Figure 4:
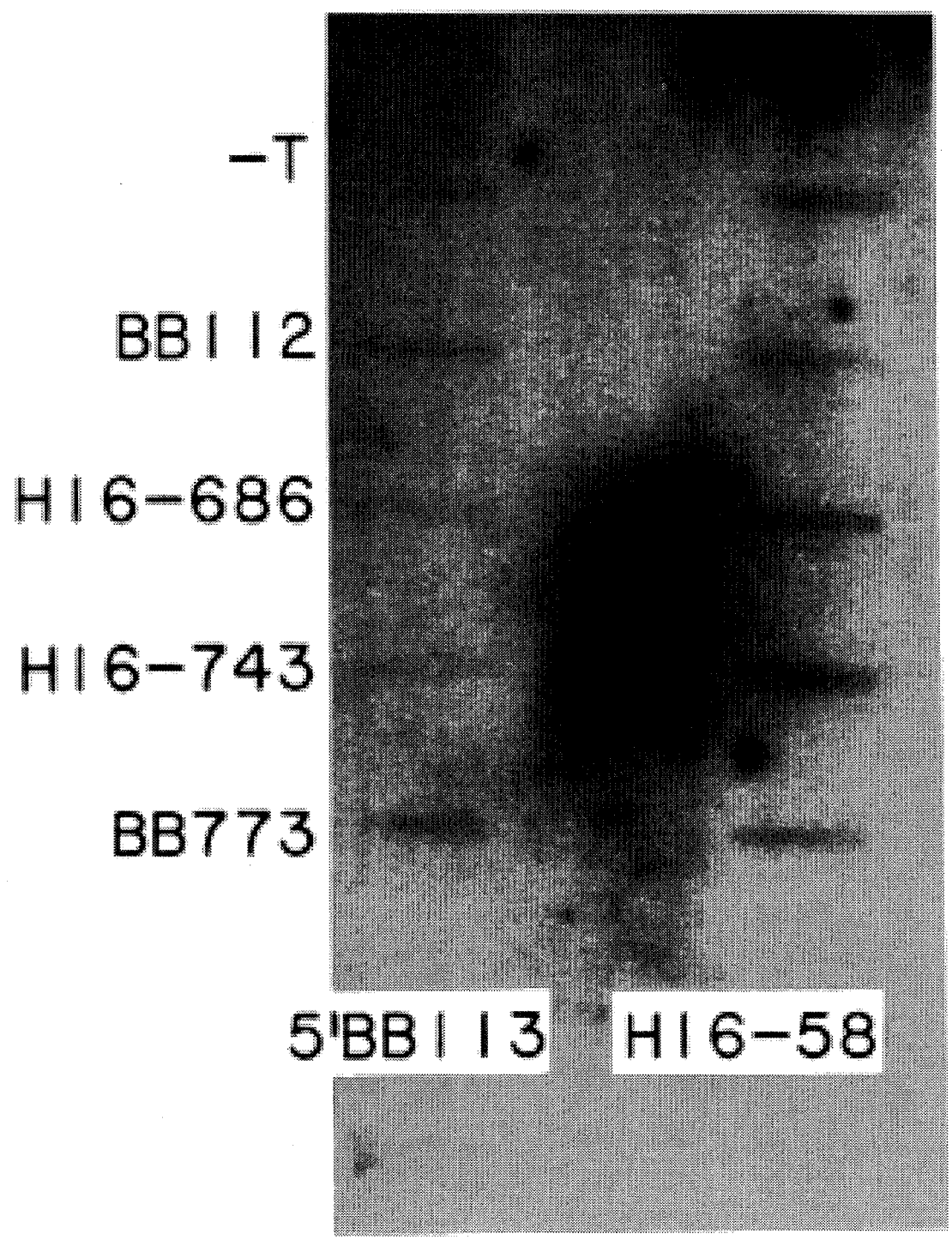
FIG. 4 is a slot blot autoradiograph of a 3SR in situ reaction with controls.

Referring to FIG. 4, primers listed in Table 1 were assayed in the 3SR reaction under standard conditions except that the amount of RNaseH was reduced from 3 units to 1 unit and DMSO (dimethylsulfoxide) was included at a concentration of 10%.

In a total volume of 100 ul, the reaction mix consisted of 20 ul 5× buffer (200 mM Tris-Cl, ph 8.1, 150 mM MgCl$_2$, 100 mM NaCl, 50 mM dithiothreitol, and 20 mM spermidine 3 HCl), 20 ul 5× nucleotide mix (35 mM of each of ATP, GTP, CTP, UTP, and 5 mM each of dATP, dGTP, dCTP, TTP), 250 mg of each primer of the chosen primer pair, 1 attomole of template RNA ($10^{-18}$ mole), and 10 ul dimethyl sulfoxide. The reaction mix was heated to 65° C. for 1 minute and cooled to 42° C. for 2 minutes. 3.5 ul of a mix of the 3SR enzymes was then added consisting of 1 ul T7 RNA polymerase (100 units), 1 ul *E. coli* RNaseH (1 unit) and 1.5 ul AMV reverse transcriptase (30 units). The reaction was incubated for 1.5 hours at 42° C. 5 ul samples of each reaction mix were subjected to slot blot analysis and using radiolabelled BB10 4 oligonucleotide as a probe for the presence of 3SR reaction products.

In column 1, BB113 was used as the 5' primer which was paired with either BB112, H16-686, H16-743, or H16-773. The results indicate that BB112 and BB773 yield significant signals above the background sample in slot #1. (This slot has a sample of a 3SR reaction run without added template.)

In the second column, a similar analysis was performed using primer H16-58 as a 5' primer. In this case, primer H16-743 yields the most significant signal above background.

These results demonstrate the importance of primer selection since this example shows not every 5' primer can support amplification with every 3' primer.

TABLE 1

| Oligonucleotides Used in 3SR In Situ Amplification | | |
|---|---|---|
| Designator | Gene | Sequence |
| *BB111 SEQ ID NO: 2 | E7 | ATG CAT GGA GAT ACA CCT ACA TTG |
| *BB112 SEQ ID NO: 3 | E7 | GCA CAA CCG AAG CGT AGA GTC ACA |
| *BB113 SEQ ID NO: 4 | E6 | ATG CAG CAA AAG AGA ACT GCA ATG |
| *BB114 SEQ ID NO: 5 | E6 | CAG CTG GGT TTC TCT ACG TGT TCT |
| H16-58 SEQ ID NO: 6 | E6 | GGA CCC ACA GGA GCG ACC CAG AAA GT |
| *H16-773 SEQ ID NO: 7 | E7 | TCT GAG AAC AGA TGG GGC ACA CAA |
| *H16-743 SEQ ID NO: 8 | E7 | GTG TGC CCA TTA ACA GGT CTT CCA |
| *H16-686 SEQ ID NO: 9 | E7 | A CAA CCG AAG CGT AGA GTC ACA CT |

| Detector | Oligonucleotides | Sequence |
|---|---|---|
| BB4 SEQ ID NO: 10 | E6 | TAA CTT TCT GGG TCG CTC CTG TGG GTC CTG |
| BB109 SEQ ID NO: 11 | E7 | ATA GAT GGT CCA GCT GGA CAA GCA GAA CCG |

TABLE 1-continued

Oligonucleotides Used in 3SR In Situ Amplification

*Contains in addition the T7 RNA Polymerase Binding site AAT TTA ATA CGA CTC ACT ATA G, noted in the Sequence Listing as SEQ ID NO: 12.
Note: All sequences were derived from the sequence of HPV 16.

EXAMPLE 2

Figure 5A:
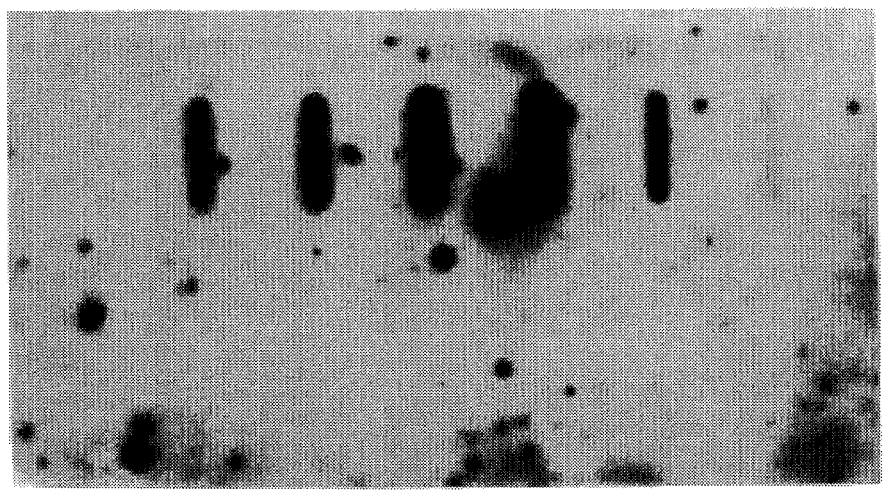
FIG. 5a is a slot blot autoradiograph of a 3SR amplification of the E6/E7 region of HPV 16.
Figure 5B:
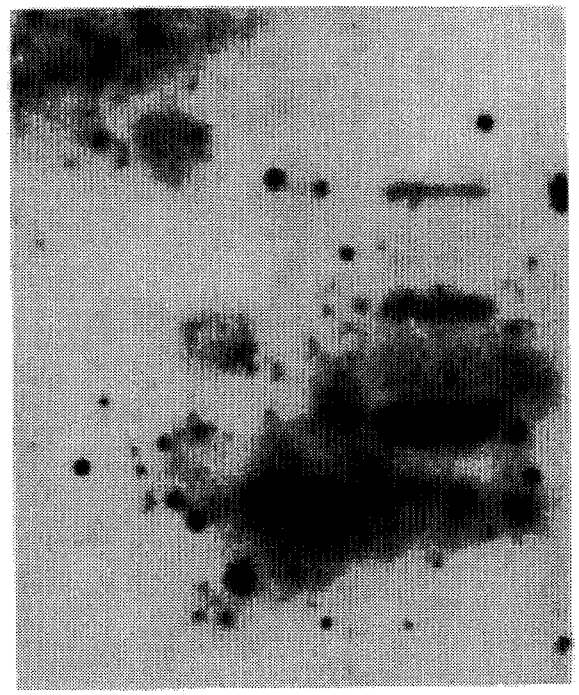
FIG. 5b is an autoradiograph showing an RNHase H titration of the 3SR Reaction.

Example 2 refers to FIG. 5A and FIG. 5B in which reaction conditions for efficient 3SR are established.

In FIG. 5A, the optimal level of RNaseH is determined. The reaction conditions are exactly as that described in Example 1 except that primers BB111/BB112 were used (see Table 1 and FIG. 3). *E. coli* RNaseH was diluted to 1, 2, 3, and 4.5 units/ul. 1 ul of each dilution was assayed in the 3SR reaction. The autoradiograph of the results of the slot blot/hybridization analysis of the 3SR products are displayed here.

The results indicate that 1 unit of RNaseH is the optimum for 3SR amplification of the HPV 16 derived RNA template used in this experiment.

In FIG. 2B, the primer pair BB113/112 is analyzed for the ability to support amplification. Primer pair BB113/BB112 will amplify the entire E6/E7 region. The reaction conditions are exactly as described in Example 1 except that primers BB113/BB112 are used, and that the reaction was supplemental with 10% glycerol of DMSO.

The results demonstrate that in the absence of additives (slot 1), very little amplification is obtained. The addition of 10% glycerol does not stimulate the reaction. However, addition of 10% DMSO does dramatically increase amplification.

The significance of this experiment is that it demonstrates the efficiency of the BB113/BB112 primer pair in the 3SR reaction under the proper conditions. DMSO is thought to unfold stable secondary structures in RNA which might inhibit 3SR amplification.

EXAMPLE 3

Figure 6A:
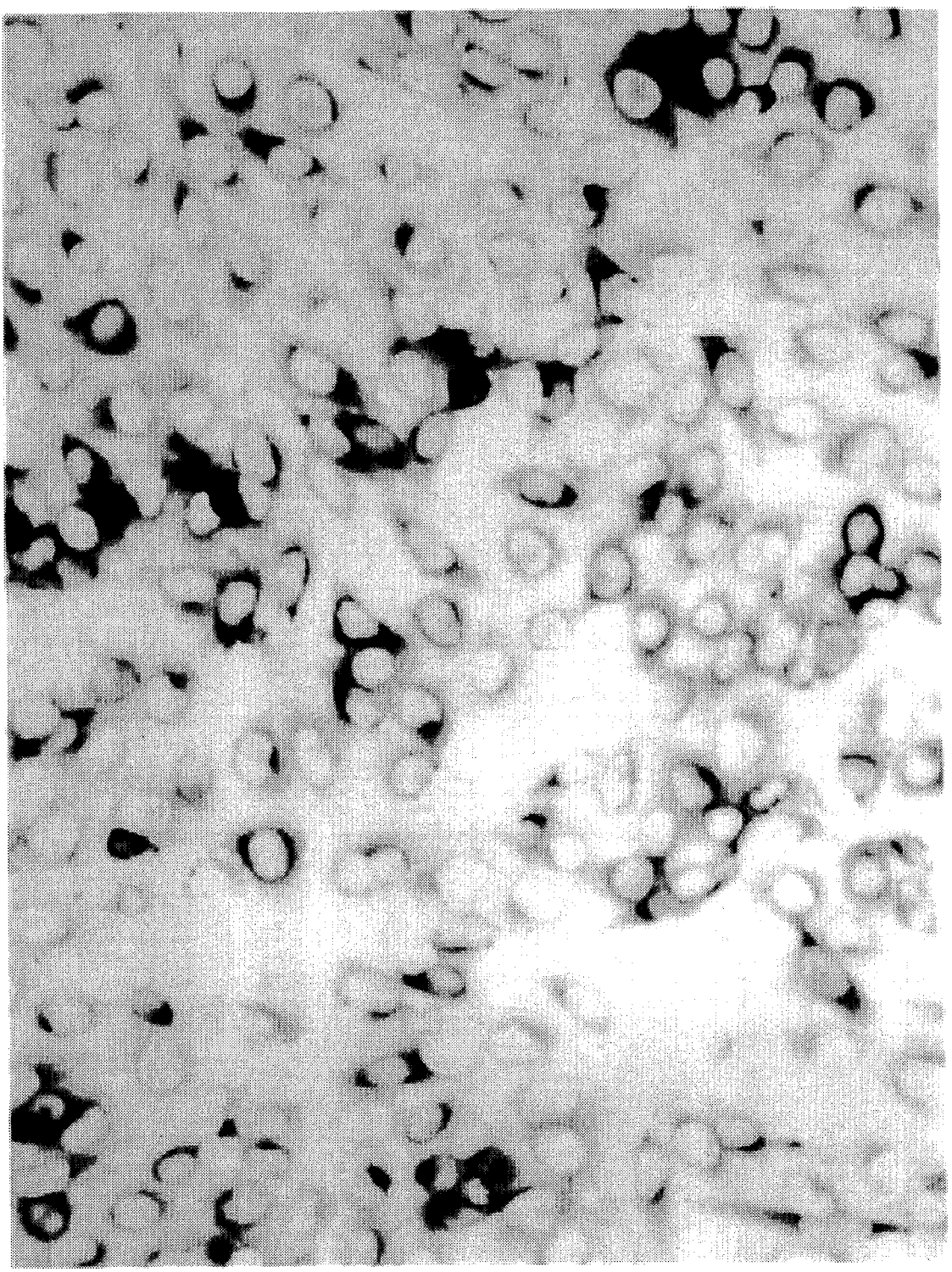
FIGS. 6a,b,c are photographs of slides showing the effect of various cell fixation conditions.
Figure 6B:
Figure 6C:
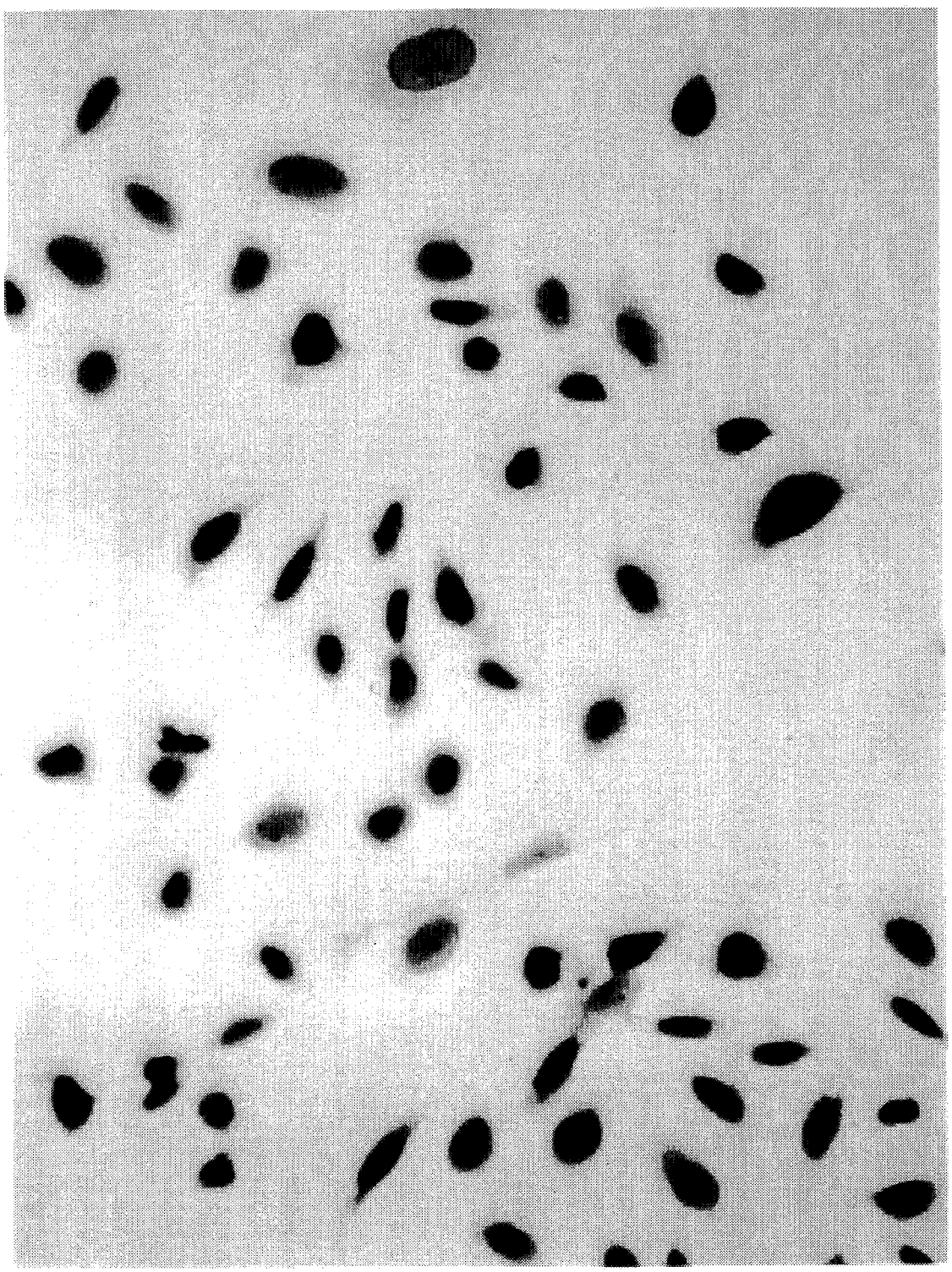

Referring to FIGS. 6A, 6B, and 6C, HPV 16 DNA was localized within cell line SiHa (containing 1–4 integrated copies of HPV 16) using probe BB4 (Table 1) conjugated to horseradish peroxidase.

SiHa cells (a cervical squamous carcinoma cell line) were grown on Lab-Tek 8 well chamber slides in (Eagles). SiHa cells were co-cultivated with human fibroblasts which act as a negative control in all experiments.

To prepare slides, media was rinsed away by two washes in PBS (phosphate buffered saline), and fixed in 4% paraformaldehyde for 10 minutes. The cells were washed with PBS again and dehydrated through an alcohol series. For in situ hybridization, cells on slides were rehydrated through the same alcohol series into 2× SSC (20× SSC=3M NaCl 0.3M sodium citrate). Cells were permeabilized by treatment with 1 ug/ml proteinase K for 10 minutes at 37° C. Proteinase K digestion was stopped by incubating the slides in 0.1M Glycine 0.1M Tris pH 7. DNA was denatured on the slides by adding 100 ul 50% formamide in 2× SSC and heating the slides to 95° C. for 1 minute. Formamide was washed away in PBS, and 100 ul of hybridization solution was added which contains 6× SSC, 5× Denhardt's (100×= 2% BSA, 2% polyvinylpyrrolidine, 2% Ficoll), 100 ug/ml single stranded nonspecific DNA, and 100 ug of HRP conjugated BB4. After 1 hour at 37° C., the slides were washed in 2× SSC at room temperature. Slides were transferred to 0.5 mg/ml diaminobenzidine, 0.1% NiCl$_2$, 0.00045% H$_2$O$_2$ for up to 15 minutes. Slides were then washed in water and incubated in silver enhancement reagent (50 g, Na$_2$CO$_3$, 2 g AgNO$_3$, 10 g tungstosilicis acid, 7 ml 40% formaldehyde, in a total of 2 liters) for up to 15 minutes. Slides were washed in 1% acetic acid, then water. Slides were counterstained in nuclear fast red, and finally dehydrated through an alcohol series, and coverslipped for observation.

This experiment demonstrates the choice of fixative in preparing cells for in situ hybridization. FIG. 6A demonstrates that when a 3:1 mix of Ethanol:Acetic acid was used, primarily enucleated cell ghosts were obtained. Likewise in FIG. 6B when 70% ethanol was used as a fixative, cell ghosts and poor retention of cellular morphology resulted. FIG. 6C demonstrates that 4% paraformaldehyde retains good cellular morphology. The pretreatments have permeablized the cells sufficiently to allow penetration of the HRP labelled BB4 probe. Also, BB4 yields a strong signal in cells which contain a very low copy number of target sequences.

EXAMPLE 4

Figure 7A:
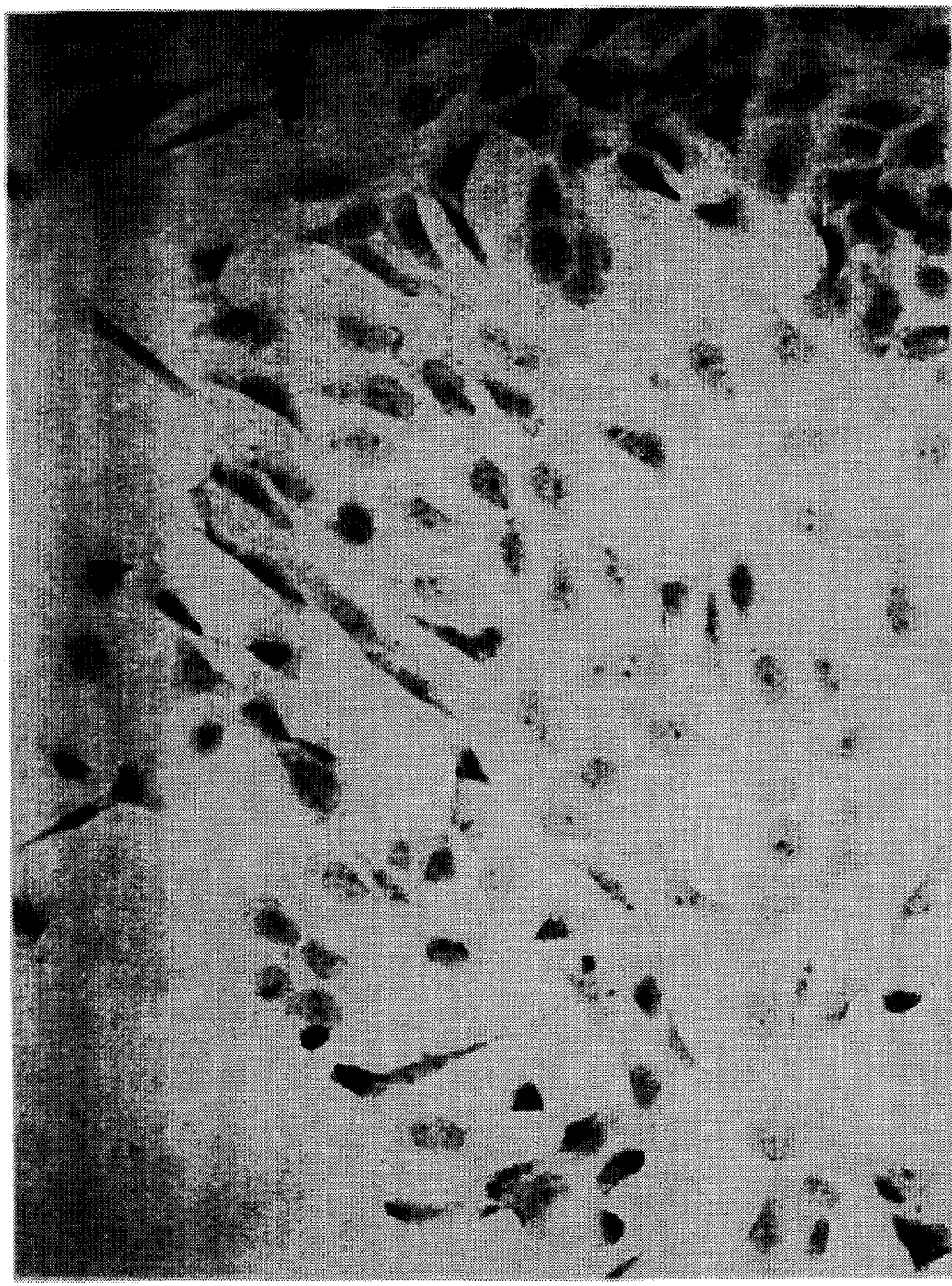
FIGS. 7a,b,c show the 3SR amplification of HPV in situ in SiHa cells.
Figure 7B:
Figure 7C:
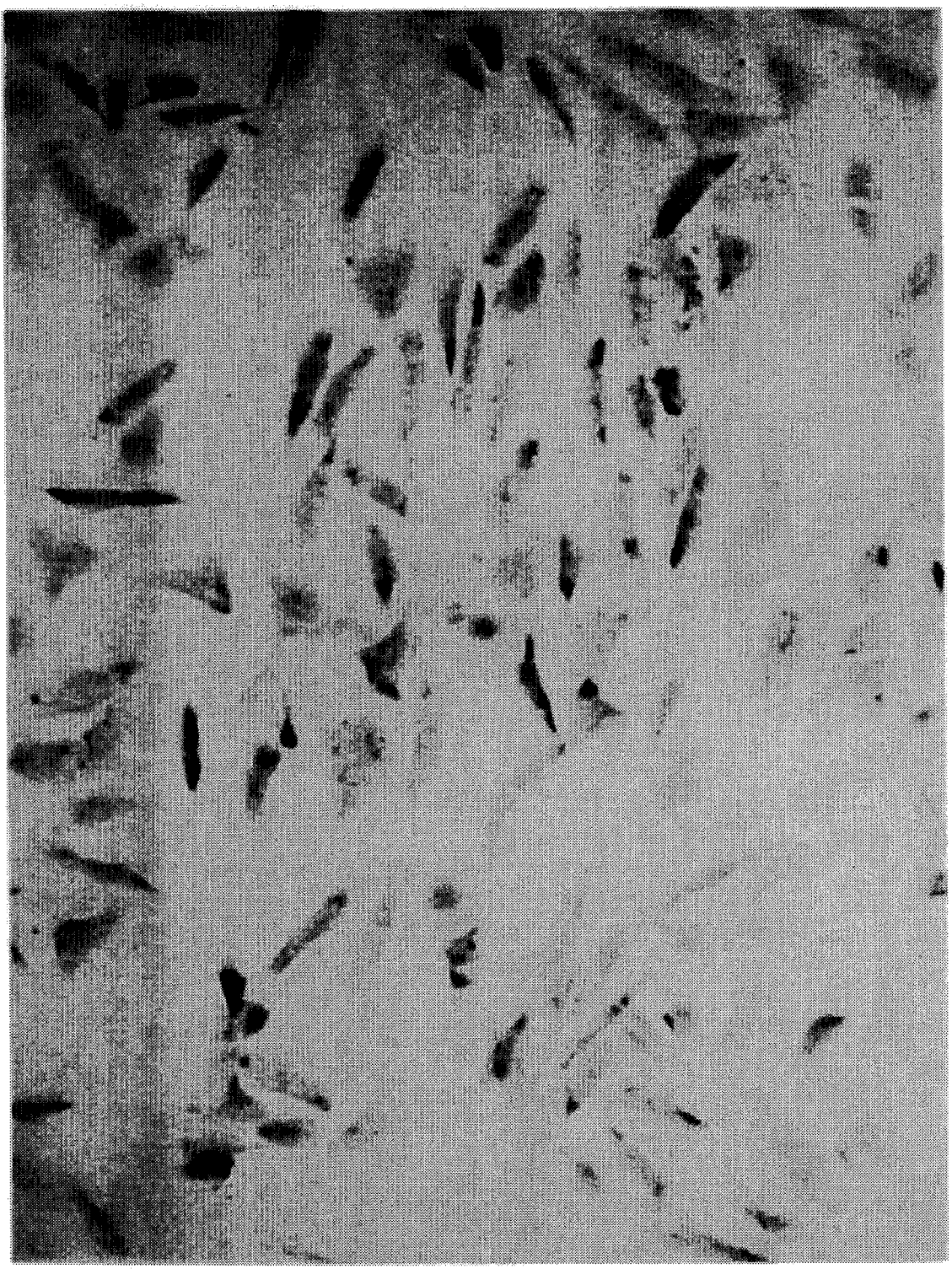

Referring to FIGS. 7A, 7B, and 7C, HPV 16 RNA was amplified in situ using the 3SR reaction.

SiHa cells were subjected to proteinase K digestion as described in Example 3. Instead of the formamide treatment, a 3SR reaction mix was added to the cells as described in Example 1. The 3SR mix contains all the components including enzymes required for 3SR amplification including primers BB113/BB112. The slides were incubated at 37° C. in a humid chamber for 2 hours. The slides were dipped briefly in 2× SSC and then in 4% paraformaldehyde for 10 minutes. Slides were rinsed in 2× SSC and hybridized with HRP labelled BB4 as in Example 3. Detection of hybridization followed exactly the procedure in Example 3.

FIG. 7A demonstrates a control reaction without added primers to determine background hybridization of BB4. Very light staining is obtained. FIG. 7B shows primers directed towards the E6 region (470 base amplified region). Some increased staining is obtained. FIG. 7C shows primers BB113/BB112 directed towards the entire E6/E7 region. In this case, strong cytoplasmic staining is obtained in SiHa cells.

The significance of this result is that in situ amplification of the E6/E7 region of HPV 16 was obtained. Table 2 summarizes the results indicated that amplification of target in the size range of 400+ bases permits visualization, but a smaller interprimer target (203 bases) does not.

TABLE 2

| Primer 1 | Primer 2 | Size of Region | Region | Amplification | Detection | Region |
|---|---|---|---|---|---|---|
| BB111* | BB112* | 203 | E7 | – | BB4 | E6 |
| BB113* | BB114* | 475 | E6 | +/– | BB109 | E7 |
| BB113* | BB112* | 678 | E6/E7 | + | BB108 | E7 |

*Contains RNA Polymerase Promoter

What is claimed is:

1. An in situ hybridization assay for detection of an intracellular marker of low copy number in cells comprising:

as a first step, fixing said cells to a support by treatment with paraformaldehyde;

next, treating said cells with a protease permeabilizing agent such that essential cell morphology is retained;

adding amplification reagents in the absence of dimethylsulfoxide comprising ribonucleotides triphosphates, an enzyme mix having reverse transcriptase and RNAse H activities, and a DNA-dependent RNA polymerase, a first primer complementary to a target RNA sequence operable to said DNA-dependent RNA polymerase, a second primer complementary to the opposite strand of said RNA target at an interval between said first and second primer of between 400 and 700 bases, and a suitable buffer, incubating said cells at a temperature of less than 50 degrees Centigrade for a time sufficient to allow amplification by self sustained sequence replication to occur, adding a labelled probe complementary to a sequence contained in the interval between said first and second primers, forming duplex images between the labelled probe and the amplified target sequence, washing the cells to remove unhybridized labelled probe, and detecting said intracellular marker of low copy number by visualization of the labelled probe target duplex images and coincident cell morphologies.

2. The assay of claim 1 wherein said target RNA sequence is an mRNA being transcribed from the E6/E7 region of the HPV genome.

* * * * *